United States Patent [19]

Garay et al.

[11] Patent Number: 5,194,003
[45] Date of Patent: Mar. 16, 1993

[54] REMOVABLE DEVICE FOR DELIVERING BENEFICIAL AGENTS ORALLY

[75] Inventors: Gabriel L. Garay, Atherton; Robert Tacy, Los Altos Hills; Anne-Ly Garay, Redwood City, all of Calif.

[73] Assignee: Transpharm Group, Inc., San Francisco, Calif.

[21] Appl. No.: 816,796

[22] Filed: Jan. 3, 1992

Related U.S. Application Data

[63] Continuation of Ser. No. 689,678, Apr. 23, 1991, abandoned, which is a continuation of Ser. No. 571,018, Aug. 22, 1990, abandoned, which is a continuation of Ser. No. 206,191, Jun. 13, 1988, abandoned.

[51] Int. Cl.⁵ .................................................. A61C 5/00
[52] U.S. Cl. ..................................... 433/215; 433/229
[58] Field of Search ..................... 433/80, 215, 229, 6

[56] References Cited

U.S. PATENT DOCUMENTS

| | | | |
|---|---|---|---|
| 1,622,616 | 3/1927 | Temple | 433/215 X |
| 1,642,653 | 9/1927 | Goldstein | 433/215 |
| 1,691,785 | 11/1928 | Remensnyder | 433/215 X |
| 2,257,709 | 9/1941 | Anderson | 433/215 X |
| 2,625,158 | 1/1953 | Lee et al. | 604/93 |
| 2,773,502 | 12/1956 | Kaslow et al. | 604/93 |
| 3,386,440 | 6/1968 | Cohen | 128/268 |
| 3,503,127 | 3/1970 | Kasdin et al. | 433/229 X |
| 3,527,219 | 9/1970 | Greenberg | 433/215 X |
| 3,600,807 | 8/1971 | Sipos | 433/229 X |
| 3,624,909 | 12/1971 | Greenberg | 433/80 |
| 3,688,406 | 9/1972 | Porter et al. | 433/80 X |
| 3,754,332 | 8/1973 | Warren | 424/435 X |
| 3,786,813 | 1/1974 | Michaels | 128/260 |
| 3,788,322 | 1/1974 | Michaels | 128/260 |
| 3,797,492 | 3/1974 | Place | 206/522 X |
| 3,901,232 | 8/1975 | Michaels et al. | 128/260 |
| 3,911,099 | 10/1975 | DeFoney et al. | 424/435 |
| 3,944,064 | 3/1976 | Bashaw et al. | 424/422 X |
| 4,039,653 | 8/1977 | DeFoney et al. | 424/435 |
| 4,055,178 | 10/1977 | Harrigan | 128/260 |
| 4,138,814 | 2/1979 | Weitzman | 433/215 |
| 4,175,326 | 11/1979 | Goodson | 433/80 |
| 4,211,008 | 7/1980 | Lerman | 433/229 |
| 4,312,347 | 1/1982 | Magoon et al. | 128/260 |
| 4,313,438 | 2/1982 | Greatbatch | 604/20 |
| 4,314,554 | 2/1982 | Greatbatch | 604/20 |
| 4,484,895 | 11/1984 | Smiley et al. | 433/215 |
| 4,485,805 | 12/1984 | Foster, Jr. | 128/1 R |
| 4,533,326 | 8/1985 | Anthony | 433/229 |
| 4,676,752 | 6/1987 | Lefkowitz | 433/229 |
| 4,685,883 | 8/1987 | Jernberg | 433/215 |
| 4,741,700 | 5/1988 | Barabe | 433/229 |
| 4,861,268 | 8/1989 | Garay et al. | 433/80 X |
| 4,892,483 | 1/1990 | Douglas, Jr. | 433/80 X |
| 4,959,052 | 9/1990 | cox | 433/80 X |
| 5,049,077 | 9/1991 | Goldin et al. | 433/80 X |
| 5,074,786 | 12/1991 | Woodward | 433/80 |

FOREIGN PATENT DOCUMENTS

| | | | |
|---|---|---|---|
| 3711912 | 10/1988 | Fed. Rep. of Germany | 433/215 |
| 8002368 | 11/1980 | PCT Int'l Appl. | 433/215 |

Primary Examiner—Gene Mancene
Assistant Examiner—Nicholas D. Lucchesi
Attorney, Agent, or Firm—Morrison & Foerster

[57] ABSTRACT

A device for delivering beneficial agents such as drugs orally for sustained time periods comprising a support member that is formfit or clasped over or around the teeth and one or more reservoir members that is/are carried on an exterior surface of the support along the labial, buccal or lingual surfaces of the teeth and is adapted to hold the agent and release it to the oral cavity for achieving a local effect within the mouth, an effect elsewhere in the gastrointestinal tract or systemically.

2 Claims, 1 Drawing Sheet

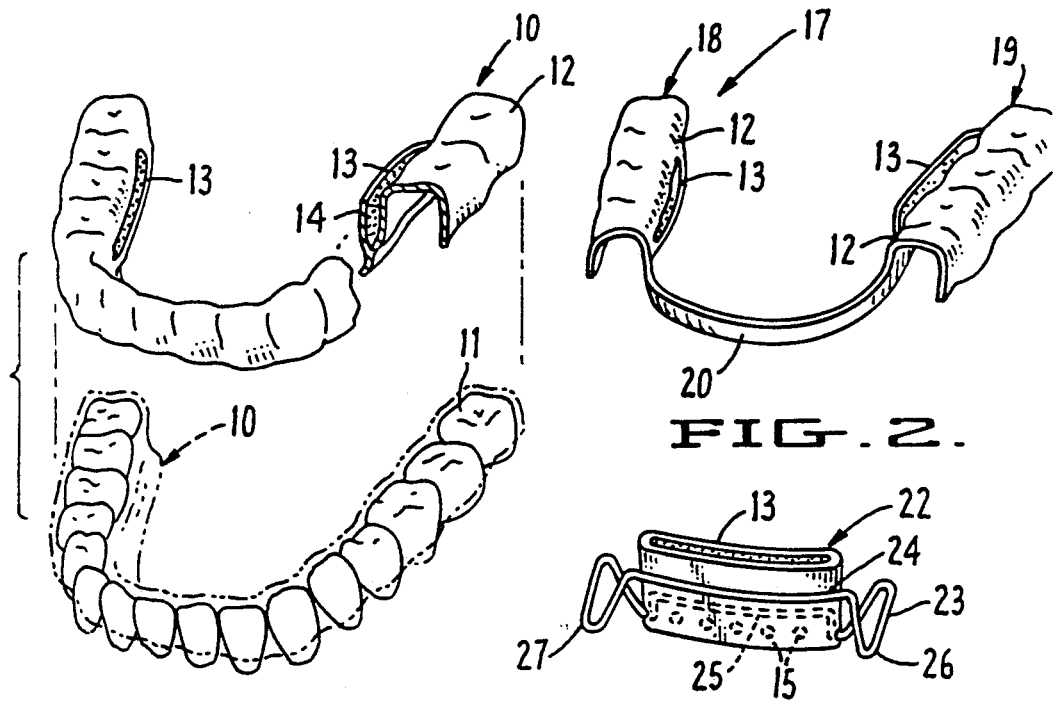
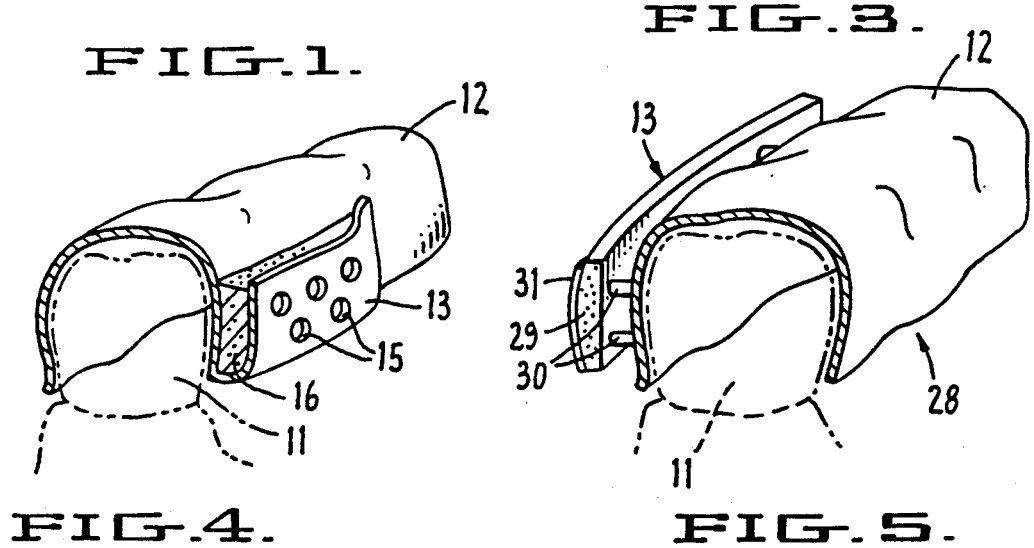

REMOVABLE DEVICE FOR DELIVERING BENEFICIAL AGENTS ORALLY

This is a continuation of application Ser. No. 07/689,678, filed Apr. 23, 1991, now abandoned, which is a continuation of application Ser. No. 07/571,018, filed Aug. 22, 1990, now abandoned, which is a continuation of application Ser. No. 07/206,191, filed Jun. 13, 1988, now abandoned.

DESCRIPTION

1. Technical Field

The invention is in the field of drug delivery. More specifically it is in the field of sustained release devices for administering drugs or other beneficial agents orally.

2. Background of the Invention

The prolonged delivery of drugs orally has been a major challenge and a long desired objective in drug therapy. This is a favored route for drug administration. It is estimated that 65% of all drugs are ingested. The successful accomplishment of prolonged oral drug delivery has great therapeutic significance in the treatment of various diseases and conditions.

Systemic and transdermal sustained drug delivery systems have been developed which are capable of delivering constant amounts of therapeutic substances from several days to several months. The major limitation to long-term oral delivery, however, is the 8-16 hour gastrointestinal transit time of an ingested substance. In order to achieve uninterrupted action for longer than 24 hours by a therapeutic substance, its passage needs to be slowed in the gastrointestinal tract or the delivery device supplying the drug has to be fixed or immobilized within the tract.

Attempts have been made either to incorporate drugs into floating devices which would empty less readily from the stomach (N. Eng. J. Med. (1981) 304:1365-1366) or to utilize insoluble bioadhesive polymers as carriers for drugs. It is thought that a delivery device made of such a polymer would adhere to the mucosa of the gastrointestinal tract and be able to discharge its contents in a sustained manner ("Advances in Drug Delivery Systems", J.M. Anderson and S.W. Kim, Eds., Elsevier, Amsterdam, Vol. 1, 1986, pp. 47-57). Although some of these approaches have had limited success in animals, they have proved to be impractical in humans thus far.

The diseases and conditions of dentition and of the oral cavity, on the other hand, have been more freely targeted for timed-release chemicals or therapeutic substances which have been placed inside delivery devices intended to act for longer than 24 hours. Considerable attention has been paid to the control of bad breath or taste in the mouth by means of dispensing deodorizers or chemicals that impart a pleasant taste or mask unpleasant odors. U.S. Pat. Nos. 3,503,127 and 3,600,807 describe inventions where a cup or pocket is formed in a denture or in an artificial tooth in order to store and make available breath- and taste-refreshing chemicals. U.S. Pat. No. 2,835,628 proposes the use of medicated tape impregnated with prolonged-release sodium fluoride. This device is made to adhere to the tooth's surface for the prevention of dental caries. In another invention a soluble tape impregnated with fluoride or other chemicals for the local treatment of oral diseases is inserted between teeth and left there to dissolve and disperse its active ingredient (U.S. Pat. No. 3,754,332).

Other inventions propose to employ biocompatible adhesives and patches in order to affix tablets directly to the buccal mucosa for odor masking, for buccal delivery of local anesthetics and antihistamines, or even for the local release of nitroglycerin (U.S. Pat. Nos. 3,911,099 and 4,039,653). However, most of these delivery systems are expected to remain fixed only for a relatively short period of time.

French Patent 2,278,317 describes a medicated tab attached to a blunt-nosed spike which can be pushed into the space between two adjacent teeth. The objective is to provide a local, sustained release of medications when the tab comes into contact with the gum line.

The use of a medicated pad placed over the open socket of a freshly extracted tooth for the relief of pain and hemorrhage was also suggested (U.S. Pat. No. 3,386,440). There is significant interest in treating gingivitis and periodontal diseases by placing long-acting medications locally in the vicinity of the inflamed gum or by introducing active substances directly into the disease-induced subgingival pockets (J. Periodontology (1984) 11:651-657).

Goodson (U.S. Pat. No. 4,175,326) discloses capillary hollow fibers filled with the antibiotic tetracycline. These hollow fiber bands are slipped over each tooth, then rolled down into the periodontal pocket in order to achieve a high local concentration of the antibiotic. The control of the local microbial flora linked to the pathogenesis of this disease is the aim of this process.

The further utilization of drug-loaded hollow fiber bands for the therapy of other oral conditions requiring the local availability of anti-inflammatory, antifungal, or immune modulator substances is also suggested. Jernberg in U.S. Pat. No. 4,685,883 describes a delivery system of biodegradable, time-release microspheres encapsulating drugs and packed tightly into the subgingival periodontal pocket. He also suggests the use of a biodegradable matrix adhesively attached to the root of the tooth for the more effective local treatment of the periodontal disease is also suggested in the patent.

U.S. Pat. No. 4,861,544 describes an oral pack retention system to hold surgical dressings over a fresh wound site in order to prevent infection and hemorrhage after oral or periodontal surgery. The pack may be impregnated with drugs such as antibiotics or analgesics. The patent extends the invention of Goodson and suggests that its system, using wires and adhesives, could retain a medicated pack at the root of a tooth for the local treatment of periodontal disease. A complex and extensive system of individually adjustable splints and wires to support the pack is described.

Since most of these oral, active-substance delivery systems target the local therapy of oral diseases, they have significant limitations as to the amount of drug which can be placed, as well as limitations in the amount of time the devices will remain in place. Furthermore, there can be difficulties when these devices need to be removed, once their active content has been discharged. Replacement for repeated administration has been particularly ignored.

The prior art is particularly devoid of devices which are designed for the sustained delivery of drugs and/or other beneficial substances for the whole body, rather than just the oral cavity. There is a need for devices which can be repeatedly replenished with active substances, are easily tolerated in the mouth, and do not interfere with speech, food mastication or oral hygiene. The present invention provides such devices.

DISCLOSURE OF THE INVENTION

The invention is a device that is adapted to be supported and held in place within the oral cavity by the teeth and/or tissues adjoining the teeth and from which a beneficial agent may be released into the oral cavity comprising:

(a) a support member that is adapted to be removably secured in place over or around one or more teeth; and (b) at least one beneficial agent reservoir that is carried on an exterior surface of the support member, extends laterally of the labial, buccal or lingual surface of the teeth, and is adapted to receive and hold the beneficial agent and release it into the oral cavity.

The invention thus provides a removable platform from which drugs or other beneficial agents may be released into the oral cavity and the gastrointestinal tract at predetermined doses and dosage regimens. The reservoir element of the device is capable of receiving and holding unit doses of agent, thus facilitating tailoring the dose, and/or dosage regimen or the administration of a multiplicity of different agents simultaneously or in a predetermined sequence. Further, the reservoir may be designed so that the unit doses can be removed and/or replaced, thus making it possible to alter or extend administration of the agent(s) at will.

The device is easily removed from the mouth should the wearer desire to do so during eating or cleaning of the teeth.

BRIEF DESCRIPTION OF THE DRAWINGS

In the drawings, which are not to scale and in which like parts are referred to by the same reference numeral:

FIG. 1 is an exploded, partially cutaway view of one embodiment of the invention device that is designed as a dental overlay to be worn on the teeth of the lower jaw.

FIG. 2 depicts another embodiment of the invention device in the form of a partial dental overlay that is worn on the rear teeth of the lower jaw.

FIG. 3 shows another embodiment of the invention device that is designed to be clipped or secured via spring action to the teeth.

FIG. 4 is a cutaway view of an invention device such as those of FIGS. 1 and 2 showing details of the structure of the reservoir element.

FIG. 5 is a cutaway view of another embodiment of the invention showing an alternative reservoir element.

DETAILED DESCRIPTION OF EMBODIMENTS SHOWN IN DRAWINGS

"Beneficial agents" as used herein is intended to include drugs, vitamins, breath deodorizers, and other chemicals or compositions that are administered orally to humans or animals to achieve a beneficial effect on the recipient. The term "drug" as used herein broadly includes physiologically and/or pharmacologically active substances for producing a local effect within the mouth or gastrointestinal tract or a systemic effect at a remote site within the body.

FIG. 1 shows a device, generally designated 10, in the form of a complete dental overlay for the teeth 11 of the lower jaw. While the device is shown as an overlay for the lower teeth it will be appreciated that the device may be designed to be worn over the upper teeth.

As shown in phantom in FIG. 1 the device is supported by the teeth and the oral tissue at the base of the teeth. The device consists of two parts: a support member 12 and one or more beneficial agent reservoirs 13 that are carried on the exterior surface (i.e., the surface facing away from the teeth). The support member is the main body of the device and interfits with the teeth/adjoining tissues so as to hold the device firmly in place. It is preferably made from a durable polymer that may be cast or otherwise molded to formfit the teeth of the wearer and otherwise conform to the oral anatomy. Thus, it may be worn for substantial periods without hindering speech or mastication.

The reservoir(s) 13 may be integral with the support member or be removably affixed thereto, such as by clips, snaps, bands, adhesives or other similar mechanisms. The reservoir may be open-ended (as seen in FIGS. 1-4) or closed or be structured to be closable. Preferably, the interior of the reservoir is sized and shaped to hold unit dose forms. For devices in the form of overlays for the lower jaw the reservoir is conveniently in the structure of an elongated pocket or channel into which the beneficial agent is placed. The pocket is defined by an outer wall 14 and the surface of the support member. Device 10 has two reservoirs located lingually and laterally of the rear teeth. It will be appreciated, however, that the device might have only one reservoir or more than two reservoirs and that the reservoirs may be positioned lingually and/or labially/buccally. The reservoir is positioned laterally along the sides of the teeth so that it is out of the way of the biting surfaces and thus protected from damage by normal movement of the teeth. As shown, it is preferable that the reservoirs be elongated in order to provide a large surface area from which the beneficial agent is released. A large release area is desired to facilitate contact with saliva.

The structure and/or composition of the outer wall 14 of the reservoir and/or the formulation of the agent within the reservoir is/are preferably such that the release of agent from the reservoir will occur over a sustained period, e.g., from one day to one year. Various mechanisms to achieve sustained release such as diffusion, osmosis, bioerosion, swelling, dissolution or combinations thereof may be employed. Accordingly, as shown in FIG. 4 the wall may have pores 15 to permit saliva to enter the pocket or channel and contact the agent or agent-release mechanism 16 within the pocket. Alternatively, and depending upon the nature of the agent release mechanism, the wall may be required to be permeable to the agent or be semipermeable to permit aqueous fluid to be imbibed into the pocket to effect agent release by an osmotic mechanism.

The agent may be in the form of a solid, gel, microcapsule, or liquid depending, again, upon the nature of the reservoir and may be neat or formulated with carriers or diluents. It may be present in the form of a multiplicity of individual dosage units to facilitate tailoring of the dose to the wearer's needs. Alternatively, a multiplicity of different agents may be contained in the reservoir(s) to achieve multi-agent administration simultaneously or in a predetermined sequence or pattern. It will be appreciated that the agent may be formulated in such a manner (e.g., in coated microcapsules) that while the formulation may be released initially in the oral cavity that the release of agent from the formulation occurs elsewhere in the gastrointestinal tract.

FIG. 2 depicts another dental overlay-type device, generally designated 17, that is supported by only a portion of the teeth of the lower jaw and the adjacent oral tissues. Such a device is suitable for essentially permanent wear because it is less likely to interfere with speech or the chewing of food than the full overlay of FIG. 1. Device 17 has two overlay end sections 18 and 19 that respectively interfit with the rear teeth of the lower jaw on either side of the mouth. Each section comprises a support member 12 and carries a reservoir 13. The two sections are connected at the inner sides of the forward ends of their support members by a thin strip 20 that is adapted to lie lingually along the base of the front teeth. Alternatively, the interconnecting strip could be designed to lie labially/buccally along the front teeth. Beneficial agent is contained within and dispensed from the reservoirs of device 17 as described with respect to the device of FIG. 1.

FIG. 3 shows yet another embodiment, designated 22, of the invention. Device 22 differs from devices 10 and 17 in the nature of its support member. The support member of device 22 has a tubular or rod-shaped body 23 that is made of plastic, metal, or other material suitable for clasping teeth and is configured into two spaced middle sections 24, 25 and two end flange sections 26, 27. The middle sections are spaced so that they may lie on opposite sides of the teeth (24 labially and 25 lingually) and the flange sections are configured to clip over the teeth in clasp- or spring-like fashion. A single reservoir 13 is carried on section 25 so that it will lie laterally along the lingual side of the teeth when the device is in position. The reservoir is equipped with pores 15 which serve the same function as those shown in the device of FIG. 4. While device 22 is designed such that the reservoir is mounted lingually, the device could, of course, be designed to have the reservoir mounted labially/buccally or to carry more than one reservoir on either or both sides of the teeth. Device 22 is easily removed and replaced by the wearer and lends itself to continuous wear because it is light weight and relatively compact.

FIG. 5 shows still another embodiment, generally designated 28, of the invention. This embodiment is a variation of the devices of FIGS. 1 and 2 and differs therefrom in the nature of the reservoir. Its reservoir consists of an elongated body 29 that is suspended in spaced and lateral relationship to support member 12 by a series of spacer posts 30 that extend outwardly from the side of the support member. Body 29 may be permanently or removably attached to the posts and may provide a container for agent or merely provide a base to which an agent-containing tape member 31 is adhered.

Other embodiments of the invention that are obvious to those of skill in the fields of drug delivery devices, orthodontics, or related fields are intended to be within the scope of the following claims.

We claim:

1. A device that is adapted to be suspended and held in place with an oral cavity including an upper jaw and lower jaw by a plurality of teeth of one of said jaws and/or tissues adjoining the teeth and from which a beneficial agent is released into the oral cavity in a sustained manner comprising:
   (a) a partial overlay comprising a first section that is form fitting to a first segment of teeth on one of said jaws, a second section that is form fitting to a second segment of teeth on said one of said jaws, said first segment being spaced from said second segment and an interconnecting middle section; and
   (b) at least one beneficial agent reservoir that is carried on an exterior surface of the partial overlay, extends laterally of the labial, buccal or lingual surface of the teeth, is adapted to hold the beneficial agent and has a multiplicity of open-agent-release orifices that permit increase of saliva into the reservoir to dissolve the agent from the reservoir.

2. The device of claim 1 wherein said first section caries a beneficial agent reservoir and said second section carries a beneficial agent reservoir.

* * * * *